(12) United States Patent
Costa et al.

(10) Patent No.: US 12,419,894 B2
(45) Date of Patent: *Sep. 23, 2025

(54) RIBOCICLIB TABLET

(71) Applicant: Novartis AG, Basel (CH)

(72) Inventors: Rui Costa, Basel (CH); Arnaud Grandeury, Helfrantzkirch (FR); Bindhumadhavan Gururajan, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/977,228

(22) Filed: Dec. 11, 2024

(65) Prior Publication Data

US 2025/0127785 A1    Apr. 24, 2025

Related U.S. Application Data

(63) Continuation of application No. 18/588,259, filed on Feb. 27, 2024, which is a continuation of application (Continued)

(51) Int. Cl.
*A61K 31/519*    (2006.01)
*A61K 9/20*      (2006.01)

(Continued)

(52) U.S. Cl.
CPC .......... *A61K 31/519* (2013.01); *A61K 9/2027* (2013.01); *A61K 9/2054* (2013.01);

(Continued)

(58) Field of Classification Search
CPC .. A61K 31/519; A61K 9/2027; A61K 9/2054; A61K 9/2077; A61K 9/284; A61K 31/496
See application file for complete search history.

(56) References Cited

U.S. PATENT DOCUMENTS 5,885,617 A      3/1999   Jordan
10,799,506 B2 *  10/2020  Gururajan ............ A61K 9/2077
(Continued)

FOREIGN PATENT DOCUMENTS

EP    2742940 A1 *   6/2014  .......... A61K 31/439
WO    2012064805 A1   5/2012
(Continued)

OTHER PUBLICATIONS

FDA CDER 1997 Document on Guidance for Industry on Dissolution Testing of Immediate Release Solid Oral Dosage Forms. (Year: 1997).*

(Continued)

*Primary Examiner* — Blessing M Fubara
(74) *Attorney, Agent, or Firm* — Derek Denhart

(57) ABSTRACT

The present disclosure is directed to oral tablet of ribociclib including its salt(s). One embodiment of the present disclosure is directed to tablet of ribociclib with high drug load with an immediate release profile. One embodiment of the present disclosure is directed to coated tablet of ribociclib. Another embodiment of the present disclosure is directed to coated tablet of ribociclib where the coating is an aqueous moisture barrier coating (e.g., Opadry® amb II coating where the coating is PVA based).

4 Claims, 5 Drawing Sheets

DVS data on the Ribociclib Tablets with standard Opadry® (aka Opadry 1, HMPC coating) and Opadry® amb II (aka Opadry 2, AMB functional coating)

Related U.S. Application Data

No. 17/805,956, filed on Jun. 8, 2022, now Pat. No. 12,064,434, which is a continuation of application No. 17/003,771, filed on Aug. 26, 2020, now abandoned, which is a continuation of application No. 15/564,534, filed as application No. PCT/IB2016/052136 on Apr. 14, 2016, now Pat. No. 10,799,506.

(60) Provisional application No. 62/148,240, filed on Apr. 16, 2015.

(51) Int. Cl.
  *A61K 9/28* (2006.01)
  *A61K 31/496* (2006.01)
(52) U.S. Cl.
  CPC ............ *A61K 9/2077* (2013.01); *A61K 9/284* (2013.01); *A61K 31/496* (2013.01)

(56) References Cited

U.S. PATENT DOCUMENTS

| | | | |
|---|---|---|---|
| 12,064,434 B2 * | 8/2024 | Costa | A61K 31/496 |
| 2011/0071185 A1 * | 3/2011 | Bunick | A61K 9/0056 264/491 |
| 2020/0390771 A1 | 12/2020 | Costa | |
| 2023/0104792 A1 | 4/2023 | Costa | |

FOREIGN PATENT DOCUMENTS

| | | | | |
|---|---|---|---|---|
| WO | WO-2014097125 A1 * | 6/2014 | | A61K 31/4184 |
| WO | 2016166703 A1 | 10/2016 | | |

OTHER PUBLICATIONS

Ando, et al., Evaluation of a novel sugar coating method for moisture protective tablets, International Journal of Pharmaceutics, 336, 319-328, 2007.
Application of Opadry in Tablet Film Coating, Chinese Journal of Pharmaceuticals, 44(2), 2013.
Augsburger, et al., Super Disintegrants: Characterization and Function, Encyclopedia of Pharmaceutical Technology, 20, 269-293, 2001.
Aulton, Pharmaceutics: The Science of Dosage Form Design, chapter 27 and 28, 397-440, 441-448, 2002.
Colorcon—Compliance assessment for Opadry AMB II 88A180040 white,© BPSI Holdings LLC, 2010 [Accessible via https://my.colorcon.com/compliance•assessment].
Embase entry for Shen, Cover Up, Innovations in Pharmaceutical Technology, 2015.
EUTCT: Opadry AMB II 88A180040 white (Colorcon) [Accessible via https:// eutct.ema.europa.eu/ eutct/], 2010, downloaded Aug. 15, 2023.
Extract from Opadry® amb II, (colorcon.com).
Felton, Film Coating of Oral Solid Dosage Forms, Encyclopedia of Pharmaceutical Technology, 1729-1747, 2007.
Fujii, et al., PVA copolymer: the new coating agent, Pharmaceutical Technology Europe, 20(10), Oct. 1, 2008.
Gennaro, et al., Oral solid dosage forms, Remington: The Science and Practice of Pharmacy, chapter 38 and 45, 704, 858-893, 2000.
Gimbel, et al., Evaluation of a Novel, PEG-free Immediate Release Opadry® Aqueous Moisture Barrier Film Coating with High Productivity, AAPS Poster Reprint, 4 pages, 2014, EP.
Giron, Characterisation of salts of drug substances, Journal of Thermal Analysis and Calorimetry, 73(2), 441-457, 2003, EP.
Joshi, et al., Film coatings for taste masking and moisture protection, International Journal of Pharmaceutics, 457, 395-406, Oct. 20, 2013.
Karuppiah, Analytical method development for dissolution release of finished solid oral dosage forms, International Journal of Current Pharmaceutical Research, 4(2), 48-53, 2012.
Koo, et al., Investigation into Stability of Poly(Vinyl Akohol)-Based Opadry® II Films, AAPS PharmSciTech, 12(2), 746-754, Jun. 2011.
Lachman, et al., The Theory and Practice of Industrial Pharmacy, The Theory and Practice of Industrial Pharmacy, chapter 8 and 9, 171-196, 301-303, 1987.
Liu, et al., Update on Polymers for Oral Drug Delivery, 2.4.2, 21-22, 2011.
Manufacturing Chemist, Colorcon adds Opadry amb II to portfolio, Mar. 10, 2015.
Novartis Annual Report 2014.
Olanich, et al., CDK4 Amplification Reduces Sensitivity to CDK4/6 Inhibition in Fusion-Positive Rhabdomyosarcoma, Clinical Cancer Research, 21(21), 4947-4959, Nov. 1, 2015.
Opadry® II, High Performance Film Coating System, Reducing Coated Tablet Defects from Laboratory through Production Scale: Performance of Hypromellose or Polyvinyl Alcohol-Based Aqueous Film Coating Systems, © Colorcon, 2009.
Opadry® II/Opadry® amb, High Performance and Aqueous Moisture Barrier Film Coating System, Use of Maximum Fluid Delivery Rate Measurements to Assess the Productivity of Moisture Barrier Film Coatings, 2011.
Opadry® amb, Aqueous Moisture Barrier Film Coating System, Coating Parameters, 2009.
Proof of Publication of Rajabi-Siahboomi, Excipient Selection in Oral Solid Dosage Formulations Containing Moisture Sensitive Drugs, 2015.
Rajabi-Siahboomi, et al., Excipient Selection in Oral Solid Dosage Formulations Containing Moisture Sensitive Drugs, Excipient Applications in Formulation Design and Drug Delivery, chapter 13, 385-421, 2015.
Rajabi-Siahboomi, et al., The Applications of Formulated Systems for the Aqueous film Coating of Pharmaceutical Oral Solid Dosage Forms, Aqueous Polymeric Coatings for Pharmaceutical Dosage Forms, chapter 11, 323-343, 2008.
Rios, A Fresh Coat: Innovation in Excipients, Pharmaceutical Technology, 32(11), Nov. 2, 2008.
Ritschel, et al., Die Tablette, chapter 1, 2, 6, 20-21, 63-73, 115-116, 123, 126-129, 478-480, 2002.
Ritschel, et al., Die Tablette, chapter 1, 30-31, 2002.
Rowe, et al., Handbook of Pharmaceutical Excipients, 2006.
Rowe, et al., Polyvinyl Alcohol, Handbook of Pharmaceutical Excipients, 564-565, 2009.
Rowe, et al., The effect of polymer molecular weight on the incidence of film cracking and splitting on film coated tablets, Journal of Pharmacy and Pharmacology, 32, 583-584, 1980.
Shen, Cover Up, Innovations in Pharmaceutical Technology, 52, 44-47, Mar. 2015.
Shen, Protection beyond the packaging, Drug Quality Insurance, 40-45, Aug. 2016.
To, et al., A Novel Method to Evaluate On-Tablet Moisture Barrier Performance of Opadry® Film Coating Systems, AAPS Poster Reprint, 2014, EP.
Vidula, et al., Regaining Control of the Cell Cycle With CDK 4/6 Inhibitors: A Promising Targeted Therapy for Breast Cancer, Journal of Targeted Therapies in Cancer, 3(4), Aug. 2014.
Zhang, et al., Antiproliferative Effects of CDK4/6 Inhibition in CDK4-Amplified Human Liposarcoma In Vitro and In Vivo, Molecular Cancer Therapeutics, 13(9), 2184-2193, Sep. 2014.
ICH Harmonised Tripartite Guideline, Stability Testing of New Drug Substances and Products Q1A(R2), Current Step 4 version dated Feb. 6, 2003, 24 pages.
Yang et al., "An Update of Moisture Barrier Coating for Drug Delivery," Pharmaceutics. 11(8):436 (16 pages), Sep. 1, 2019.
The United States Pharmacopeial Convention; Stage 6 Harmonization, Dec. 1, 2011, 8 pgs.

* cited by examiner

FIG. 1A Process flow diagram
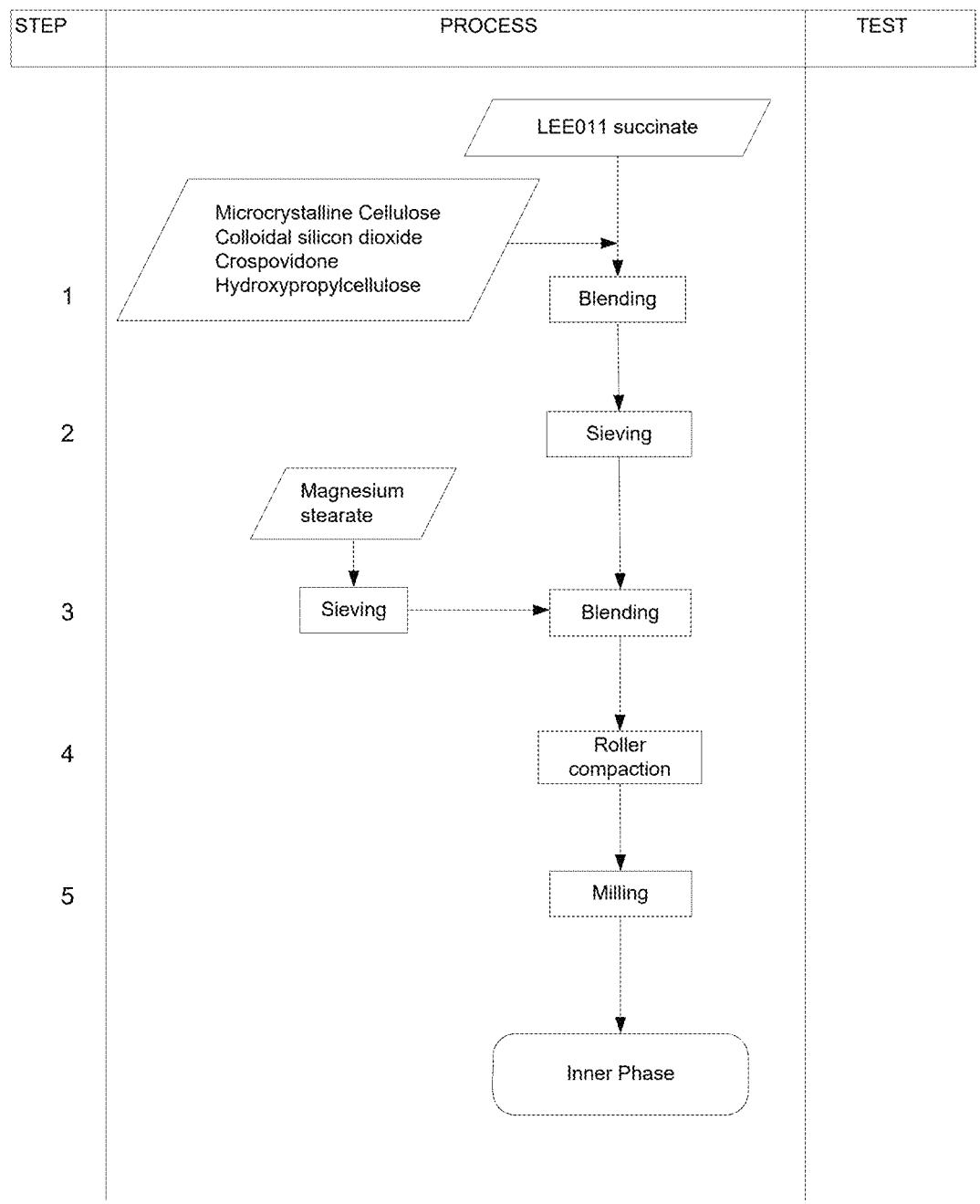

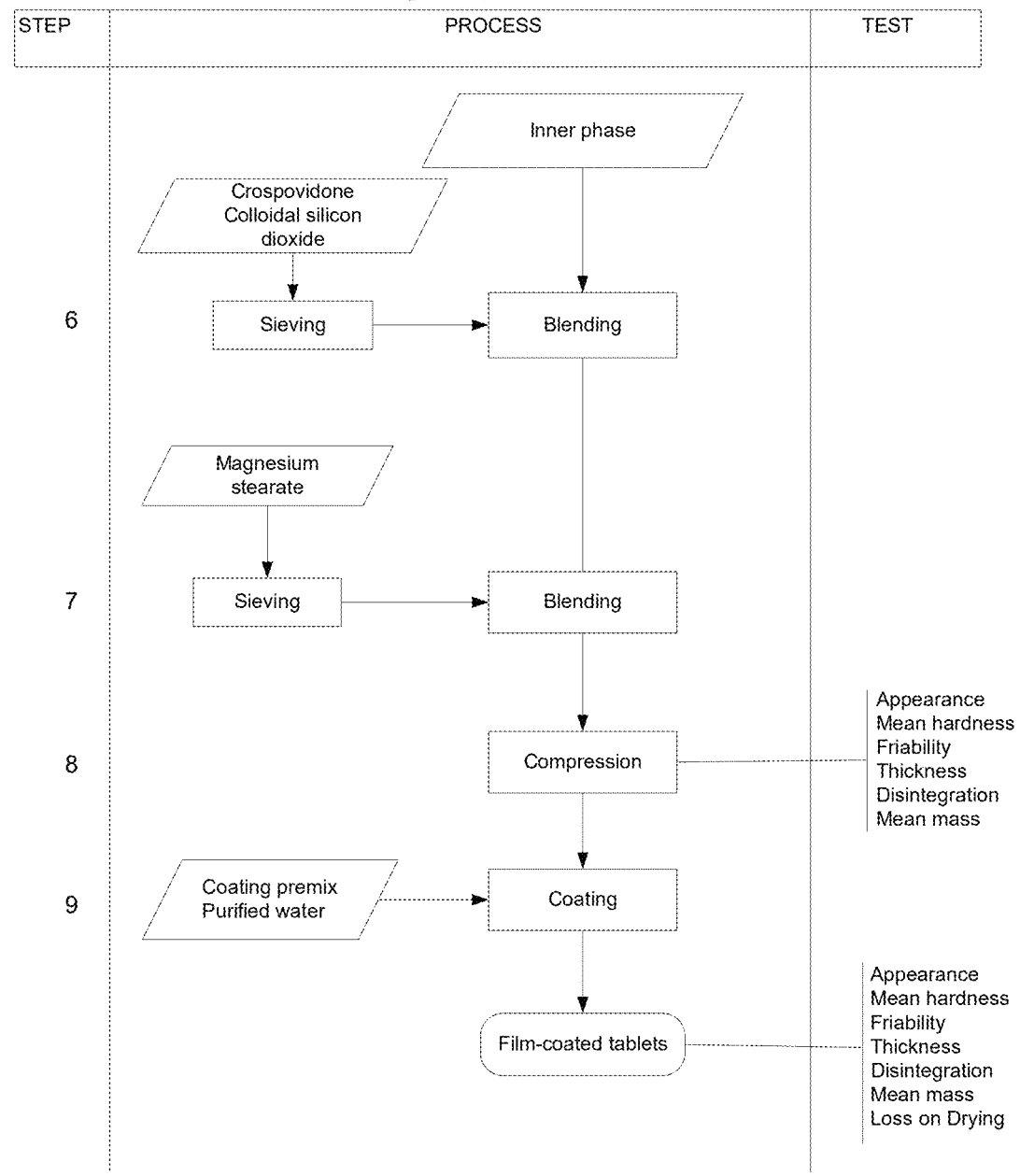
FIG. 1B   Process flow diagram (Continued)

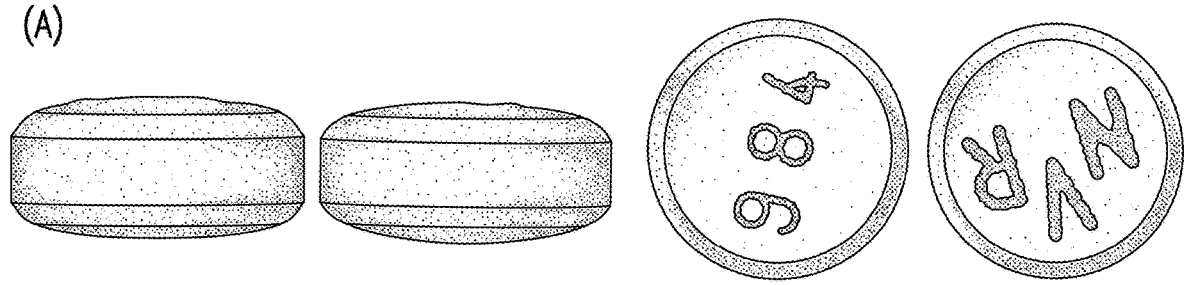
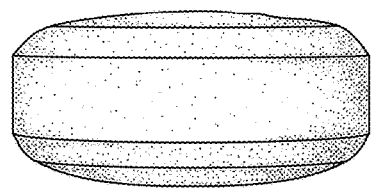
(A) Tablet with Opadry® (Standard HPMC);
(B) Tablet with Opadry® amb II (with AMB coating, PVA based)
FIG.2

FIG. 3  DVS data on the Ribociclib Tablets with standard Opadry® (aka Opadry 1, HMPC coating) and Opadry® amb II (aka Opadry 2, AMB functional coating)
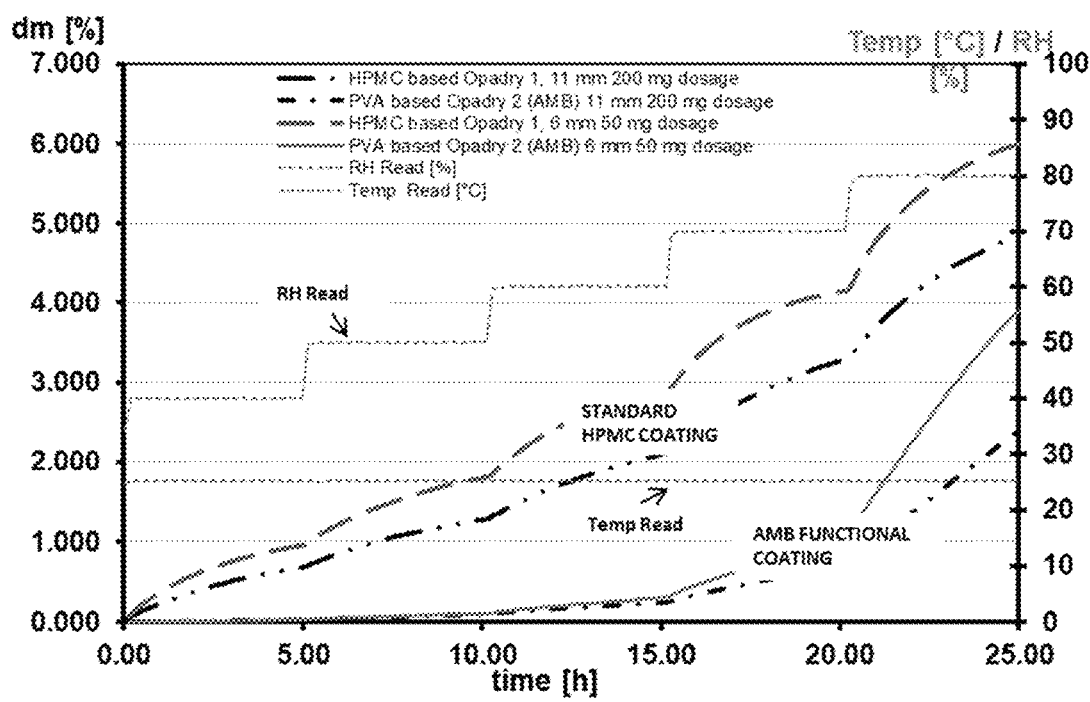

FIG. 4 Dissolution profile of Ribociclib (LEE011) tablets coated with Opadry® amb II
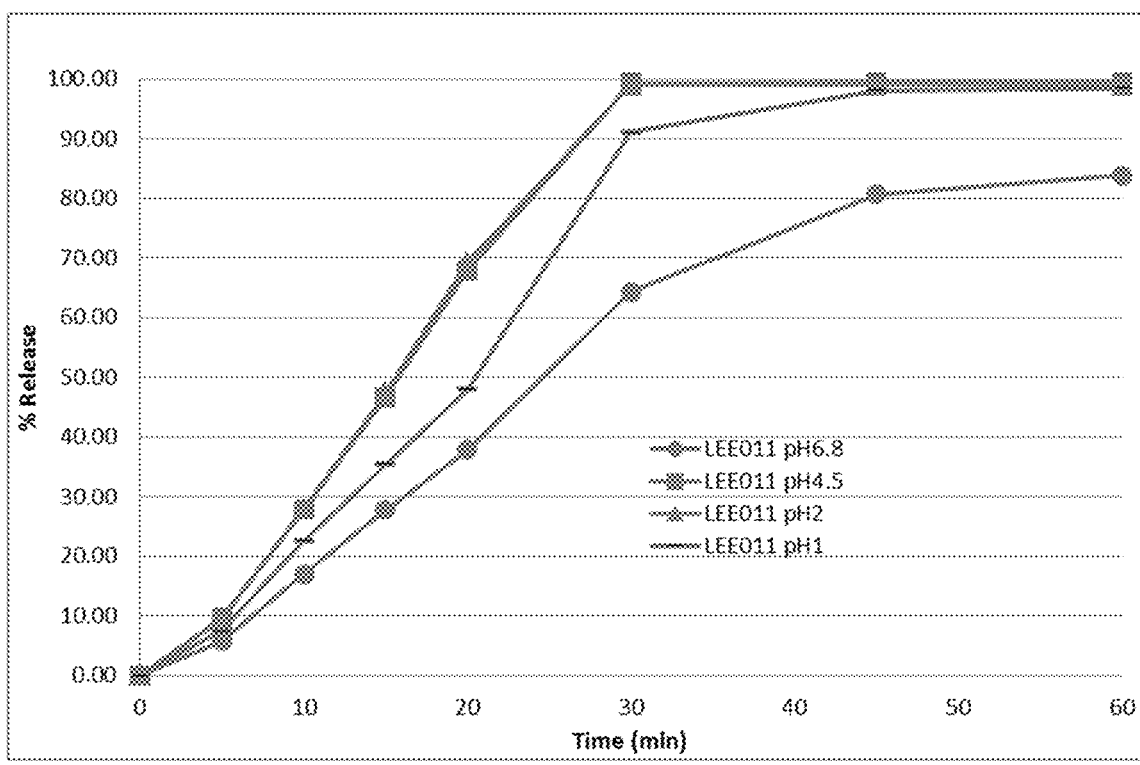

RIBOCICLIB TABLET

FIELD OF THE INVENTION

The present disclosure relates to tablet formulation of ribociclib and/or its pharmaceutically acceptable salts, as well as methods of treatment using the same.

BACKGROUND ART

The compound of Formula (I)

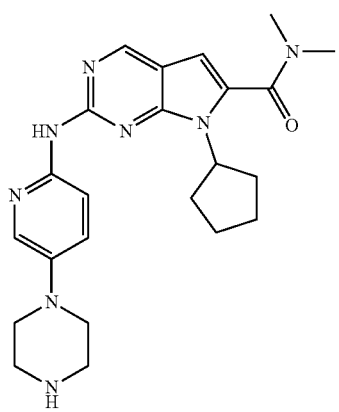

(I)

is known as ribociclib. Its chemical name is 7-cyclopentyl-N,N-dimethyl-2-{[5-(piperazin-1-yl) pyridin-2-yl]amino}-7H-pyrrolo[2,3-d]pyrimidine-6-carboxamide and its synthesis is specifically described in WO 2010/020675 A1, Example 74.

The succinate salt of ribociclib is described by Formula (II):

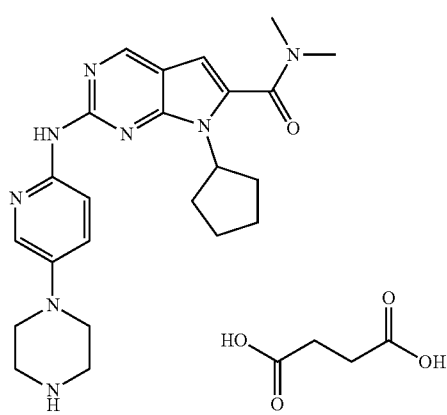

(II)

and is described in WO2012/064805.

Ribociclib and its pharmaceutically acceptable salt(s) have valuable pharmacological properties and can be used, for example, (1) as inhibitors of cyclin dependent kinases, (in particular, cyclin dependent kinases selected from CDK1, CDK2, CDK3, CDK4, CDK5, CDK6 and CDK9); and (2) as modulators and/or inhibitors of glycogen synthase kinase-3 (GSK-3).

Ribociclib is also known under the code name LEE011.

SUMMARY OF THE INVENTION

The present disclosure is directed to oral formulations of ribociclib including its salt(s) and/or solvate(s). One embodiment of the present disclosure is directed to tablet formulations of ribociclib with high drug load with an immediate release profile. One embodiment of the present disclosure is directed to coated tablet formulations of ribociclib. Another embodiment of the present disclosure is directed to coated tablet formulations of ribociclib where the coating is an aqueous moisture barrier coating (e.g., Opadry® amb II coating where the coating is PVA based).

BRIEF DESCRIPTION OF THE DRAWINGS

The invention is illustrated by reference to the accompanying drawing described below.

FIGS. 1A and 1B depict a process flow diagram for making ribociclib tablets. Uncoated tablets are made according to Steps 1-8. Coated tablets are made according to Steps 1-9.

FIG. 2 shows the images of the tablets manufactured with Opadry® (standard HPMC based) and with Opadry® amb II (aqueous moisture barrier (AMB) coating material with PVA based).

FIG. 3. shows the Dynamic Vapor Sorption (DVS) data of the ribociclib tablets coated with standard Opadry® and Opadry® amb II.

FIG. 4 shows the dissolution profile of ribociclib (LEE011) tablets coated with Opadry® amb II obtained with the rotating basket at 100 rpm with dissolution media having different pH values, at 37° C.

DETAILED DESCRIPTION OF THE INVENTION

The present disclosure relates to a solid oral tablet dosage form of ribociclib or its pharmaceutically acceptable salt. Such formulation has very good process performance and high stability.

The tablet of the present disclosure has an immediate release profile. These tablets release at least 75% (Q) (where Q refers to the acceptance criteria defined by USP chapter <711>) of the active after 45 minutes under standard dissolution test. In embodiment, the tablets release at least 75% of the active after 45 minutes when using the rotating basket at 100 rpm, with 900 ml of HCl pH 1 as dissolution medium at 37° C. In another embodiment, the tablets release at least 75% of the active after 45 minutes when using the rotating basket at 100 rpm, with 900 ml of HCl pH 2 as dissolution medium at 37° C. In another embodiment, the tablets release at least 75% of the active after 45 minutes when using the rotating basket at 100 rpm, with 900 ml of acetate buffer pH 4.5 as dissolution medium at 37° C. In another embodiment, the tablets release at least 75% of the active after 45 minutes when using the rotating basket at 100 rpm, with 900 ml of phosphate buffer pH 6.8 as dissolution medium at 37° C.

The tablets of the present disclosure can be coated or uncoated.

The tablets of the present disclosure have high drug load of at least 40%, 45%, 50%, 55% or 60%, when measured in w/w percentage of the ribociclib succinate of the core tablet.

The tablets of the present disclosure have high drug load of at least 32%, 40%, 44%, 47% or 52%, when measured in w/w percentage of the ribociclib free base of the core tablet.

The % of ribociclib succinate (w/w) is at least 40% of the core tablet. In one embodiment, the % of ribociclib succinate (w/w) is at least 50% of the core tablet. In another embodiment, the % of ribociclib succinate (w/w) is at least 55% of the core tablet. In another embodiment, the % of ribociclib succinate (w/w) is at about 55% to 65% of the core tablet. In another embodiment, the % of ribociclib succinate (w/w) is at about 60% of the core tablet.

When measured in terms of ribociclib free base, the % of ribociclib (w/w) is at least 32% of the core tablet. In one embodiment, the % of ribociclib (w/w) is at least 40% of the core tablet. In another embodiment, the % of ribociclib (w/w) is at least 44% of the core tablet. In another embodiment, the % of ribociclib (w/w) is at about 44% to 52% of the core tablet. In another embodiment, the % of ribociclib (w/w) is at about 47% of the core tablet.

Core tablet is also referred to as "tablet core".

In an uncoated tablet, the tablet core is the whole tablet. In a coated tablet, the tablet core is the portion of the tablet excluding the coating.

The tablet formulation according to the disclosure may contain pharmaceutically acceptable excipients commonly used in pharmaceutical formulations, particularly those for oral administration for example, as fillers, binders, disintegrants and lubricants.

Fillers, for example, can be cellulose, mannitol, di-calcium phosphate, lactose, microcrytalline cellulose, alone or in combination thereof.

Binders, for example, can be hydroxypropyl cellulose, polyvinyl-pyrrolidone, alone or in combination thereof.

Disintegrants, for example, can be crosslinked polyvinyl-pyrrolidone, crosslinked sodium carboxymethyl cellulose, low substituted hydroxypropyl cellulose, sodium starch glycolate, alone or in combination thereof.

Lubricants, for example, can be magnesium stearate, stearic acid, talc, silicon dioxide, sodium stearyl fumarate, alone or in combination thereof.

As an example, FIGS. 1A and 1B show the process flow diagram of making ribociclib tablets. Uncoated tablets are made according to Steps 1-8. Coated tablets are made according to Steps 1-9.

In one embodiment, the core ribociclib tablets have an inner phase comprising ribociclib or salt(s) thereof, and an outer phase.

Coating Material:

The ribociclib tablets of the present disclosure are immediate release tablets and can be coated with any immediate release coating materials. For example, the coating material can be Opadry®, Opadry® 200, Opadry® amb II, Opadry® Fx™, Opadry® II, Opalux®, or mixtures thereof. Opadry®, Opadry® 200, Opadry® amb II, Opadry® Fx™, Opadry® II, and Opalux® are all commercially available through Colorcon, Inc.

In one embodiment, the coating material is Opadry®. Opadry® is a HPMC (hydroxypropyl methylcellulose) coating material and has the following composition: HPMC (Pharmacoat 603) 71.4%, polyethylene glycol 7.15%, talc 7.15%, and iron oxide 14.3%.

In another embodiment, the coating material is Opadry® amb II. Opadry® amb II is a PVA (polyvinyl alcohol) based coating material and has the following composition: polyvinyl alcohol 45.52%, iron oxide 32%, talc 20%, lecithin (soya) 2%, and xanthan gum 0.48%.

When the ribociclib tablets are coated with Opadry® amb II, the tablets show improved appearances and are essentially free of cracking defects.

The present invention(s) is further described in the following example. The following non-limiting examples illustrate the invention(s) and are not to be construed as limiting the scope of the appended claims.

Example 1 Uncoated 50 mg and 200 mg Ribociclib Tablets

Table 1 below details the composition of uncoated 50 mg and 200 mg ribociclib tablets. These tablets are made according to Steps 1-8 of the process flow diagram (FIGS. 1A-1B).

TABLE 1

Composition per dosage form unit

| | Composition per unit [mg/unit] | |
|---|---|---|
| Ingredient | 50 mg of Ribociclib | 200 mg of Ribociclib |
| Inner phase | | |
| Ribociclib (LEE011) succinate[1] | 63.600 | 254.40 |
| Microcrystalline cellulose/ Cellulose, microcrystalline | 16.860 | 67.44 |
| Hydroxypropylcellulose | 12.030 | 48.12 |
| Crospovidone | 7.300 | 29.20 |
| Colloidal silicon dioxide/Silica, colloidal anhydrous | 0.530 | 2.12 |
| Magnesium stearate[2] | 1.590 | 6.36 |
| Outer phase | | |
| Crospovidone | 3.210 | 12.84 |
| Colloidal silicon dioxide/Silica, colloidal anhydrous | 0.265 | 1.06 |
| Magnesium stearate[2] | 2.115 | 8.46 |
| Tablet weight | 107.500 | 430.00 |

[1]The salt factor is 1.272. The drug substance quantity is increased if the content is ≤99.5% with a corresponding reduction in the microcrystalline cellulose content.
[2]Vegetable origin Example 2 Uncoated 100 mg, 150 mg and 300 mg Ribociclib Tablets Table 2 below details the composition of uncoated 100 mg, 150 mg, and 300 mg ribociclib tablets. These tablets are made according to Steps 1-8 of the process flow diagram (FIGS. 1A-1B).

TABLE 2

Composition per dosage form unit

| | Composition per unit [mg/unit] | | |
|---|---|---|---|
| Ingredient | 100 mg of Ribociclib | 150 mg of Ribociclib | 300 mg of Ribociclib |
| Inner phase | | | |
| Ribociclib (LEE011) succinate[1] | 127.2 | 190.8 | 381.6 |
| Microcrystalline cellulose/ Cellulose, microcrystalline | 33.72 | 50.58 | 101.16 |
| Hydroxypropylcellulose | 24.06 | 36.09 | 72.18 |
| Crospovidone | 14.60 | 21.9 | 43.8 |
| Colloidal silicon dioxide/ Silica, colloidal anhydrous | 1.06 | 1.59 | 3.18 |
| Magnesium stearate[2] | 3.18 | 4.77 | 9.54 |
| Outer phase | | | |
| Crospovidone | 6.420 | 9.63 | 19.26 |
| Colloidal silicon dioxide/ | 0.53 | 0.795 | 1.59 |

TABLE 2-continued

Composition per dosage form unit

| Ingredient | Composition per unit [mg/unit] | | |
|---|---|---|---|
| | 100 mg of Ribociclib | 150 mg of Ribociclib | 300 mg of Ribociclib |
| Silica, colloidal anhydrous | | | |
| Magnesium stearate[2] | 4.23 | 6.345 | 12.69 |
| Tablet weight | 215.00 | 322.5 | 645.00 |

[1]The salt factor is 1.272. The drug substance quantity is increased if the content is ≤99.5% with a corresponding reduction in the microcrystalline cellulose content.
[2]Vegetable origin

Example 3 Coated (with Opadry® Amb II Coating) 50 mg and 200 mg Ribociclib Tablets Table 3 below details the composition of film-coated 50 mg and 200 mg ribociclib tablets. These tablets were made according to Steps 1-9 of the process flow diagram (FIGS. 1A-1B). The coating material is Opadry® amb II, which is commercially available and is an aqueous moisture barrier (AMB) coating, PVA based.

TABLE 3

Composition per dosage form unit

| Ingredient | Composition per unit [mg/unit] | |
|---|---|---|
| | 50 mg of Ribociclib | 200 mg of Ribociclib |
| Inner phase | | |
| Ribociclib (LEE011) succinate[1] | 63.600 | 254.40 |
| Microcrystalline cellulose/ Cellulose, microcrystalline | 16.860 | 67.44 |
| Hydroxypropylcellulose | 12.030 | 48.12 |
| Crospovidone | 7.300 | 29.20 |
| Colloidal silicon dioxide/Silica, colloidal anhydrous | 0.530 | 2.12 |
| Magnesium stearate[2] | 1.590 | 6.36 |
| Outer phase | | |
| Crospovidone | 3.210 | 12.84 |
| Colloidal silicon dioxide/Silica, colloidal anhydrous | 0.265 | 1.06 |
| Magnesium stearate[2] | 2.115 | 8.46 |
| Core tablet weight | 107.500 | 430.00 |
| Coating[3] | | |
| Coating premix, white[4] | 0.774 | 3.096 |
| Coating premix, yellow[4] | 2.537 | 10.148 |
| Coating premix, red[4] | 0.774 | 3.096 |
| Coating premix, black[4] | 0.215 | 0.860 |
| Purified water[5] | Qs | Qs |
| Film coated tablet weight | 111.800 | 447.20 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing

Example 4 Coated (with Opadry® Amb II Coating) 100 mg, 150 mg and 300 mg Ribociclib Tablets Table 4 below details the composition of film-coated 100 mg, 150 mg and 300 mg ribociclib tablets. These tablets are made according to Steps 1-9 of the process flow diagram (FIGS. 1A-1B). The coating material is Opadry® amb II, which is commercially available and is an aqueous moisture barrier (AMB) coating, PVA based.

TABLE 4

Composition per dosage form unit

| Ingredient | Composition per unit [mg/unit] | | |
|---|---|---|---|
| | 100 mg of Ribociclib | 150 mg of Ribociclib | 300 mg of Ribociclib |
| Inner phase | | | |
| Ribociclib (LEE011) succinate[1] | 127.2 | 190.8 | 381.6 |
| Microcrystalline cellulose/ Cellulose, microcrystalline | 33.72 | 50.58 | 101.16 |
| Hydroxypropylcellulose | 24.06 | 36.09 | 72.18 |
| Crospovidone | 14.60 | 21.9 | 43.8 |
| Colloidal silicon dioxide/ Silica, colloidal anhydrous | 1.06 | 1.59 | 3.18 |
| Magnesium stearate[2] | 3.18 | 4.77 | 9.54 |
| Outer phase | | | |
| Crospovidone | 6.420 | 9.63 | 19.26 |
| Colloidal silicon dioxide/ Silica, colloidal anhydrous | 0.53 | 0.795 | 1.59 |
| Magnesium stearate[2] | 4.23 | 6.345 | 12.69 |
| Core tablet weight | 215.00 | 322.5 | 645.00 |
| Coating[3] | | | |
| Coating premix, white[4] | 1.548 | 2.322 | 4.644 |
| Coating premix, yellow[4] | 5.074 | 7.611 | 15.222 |
| Coating premix, red[4] | 1.548 | 2.322 | 4.644 |
| Coating premix, black[4] | 0.43 | 0.645 | 1.29 |
| Purified water[5] | Qs | qs | qs |
| Film coated tablet weight | 223.6 | 335.4 | 670.8 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing

Example 5

Ribociclib tablets coated with different coatings (Opadry® (standard HPMC based) vs. Opadry® amb II (aqueous moisture barrier (AMB) coating material, PVA based)) were compared. Coating was carried out in Bohle coater 1 Kg scale with spray rate of 3 g/min. With standard Opadry® coating, tablet logo bridging issue and tablet cracking defects were observed. In contrast, no cracking was observed with the PVA based Opadry® amb II coated tablets.

FIG. 2 shows the images of the tablets manufactured with Opadry® (standard HPMC based) and with Opadry® amb II (aqueous moisture barrier (AMB) coating material with PVA based).

Example 6

Dynamic vapor sorption (DVS) data on the ribociclib tablets coated with standard Opadry® and Opadry® amb II are presented in FIG. 3. At both 50 mg and 200 mg dosage unit, the tablets coated with the AMB coating (Opadry® amb II) show better performance than the standard Opadry® tablets.

Example 7

The dissolution profiles of the Opadry® amb II coated ribociclib tablets are evaluated in different pH media. Apparatus: basket, Rotation: 100 rpm, Volume: 900 mL, Media: HCl pH 1, HCl pH 2, acetate buffer pH 4.5, phosphate buffer pH 6.8. FIG. 4 shows the dissolution profile of the Opadry® amb II film-coated ribociclib tablet in different pH media.

Example 8 Coated (with Opadry® Amb II Coating) 50 mg and 200 mg Ribociclib Tablets with Different Coating Premix Combination Table 5 below details the composition of film-coated 50 mg and 200 mg ribociclib tablets with different coating premix combination compared to Example 3. These tablets were made according to Steps 1-9 of the process flow diagram (FIGS. 1A-1B). The coating material is Opadry® amb II, which is commercially available and is an aqueous moisture barrier (AMB) coating, PVA based.

TABLE 5

Composition per dosage form unit

| Ingredient | Composition per unit [mg/unit] | |
|---|---|---|
| | 50 mg of Ribociclib | 200 mg of Ribociclib |
| Inner phase | | |
| Ribociclib (LEE011) succinate[1] | 63.600 | 254.40 |
| Microcrystalline cellulose/ Cellulose, microcrystalline | 16.860 | 67.44 |
| Hydroxypropylcellulose | 12.030 | 48.12 |
| Crospovidone | 7.300 | 29.20 |
| Colloidal silicon dioxide/Silica, colloidal anhydrous | 0.530 | 2.12 |
| Magnesium stearate[2] | 1.590 | 6.36 |
| Outer phase | | |
| Crospovidone | 3.210 | 12.84 |
| Colloidal silicon dioxide/Silica, colloidal anhydrous | 0.265 | 1.06 |
| Magnesium stearate[2] | 2.115 | 8.46 |
| Core tablet weight | 107.500 | 430.00 |
| Coating[3] | | |
| Coating premix, white[4] | 4.201 | 16.804 |
| Coating premix, red[4] | 0.037 | 0.146 |
| Coating premix, black[4] | 0.062 | 0.25 |
| Purified water[5] | Qs | Qs |
| Film coated tablet weight | 111.800 | 447.20 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing Example 9 Coated (with Opadry® Amb II Coating) 100 mg, 150 mg and 300 mg Ribociclib Tablets with Different Coating Premix Combination Table 6 below details the composition of film-coated 100 mg, 150 mg and 300 mg ribociclib tablets with different coating premix combination compared to Example 4. These tablets are made according to Steps 1-9 of the process flow diagram (FIGS. 1A-1B). The coating material is Opadry® amb II, which is commercially available and is an aqueous moisture barrier (AMB) coating, PVA based.

TABLE 6

Composition per dosage form unit

| Ingredient | Composition per unit [mg/unit] | | |
|---|---|---|---|
| | 100 mg of Ribociclib | 150 mg of Ribociclib | 300 mg of Ribociclib |
| Inner phase | | | |
| Ribociclib (LEE011) succinate[1] | 127.2 | 190.8 | 381.6 |
| Microcrystalline cellulose/ Cellulose, microcrystalline | 33.72 | 50.58 | 101.16 |
| Hydroxypropylcellulose | 24.06 | 36.09 | 72.18 |
| Crospovidone | 14.60 | 21.9 | 43.8 |
| Colloidal silicon dioxide/ Silica, colloidal anhydrous | 1.06 | 1.59 | 3.18 |
| Magnesium stearate[2] | 3.18 | 4.77 | 9.54 |
| Outer phase | | | |
| Crospovidone | 6.420 | 9.63 | 19.26 |
| Colloidal silicon dioxide/ Silica, colloidal anhydrous | 0.53 | 0.795 | 1.59 |
| Magnesium stearate[2] | 4.23 | 6.345 | 12.69 |
| Core tablet weight | 215.00 | 322.5 | 645.00 |
| Coating[3] | | | |
| Coating premix, white[4] | 8.402 | 12.603 | 25.206 |
| Coating premix, red[4] | 0.074 | 0.111 | 0.222 |
| Coating premix, black[4] | 0.124 | 0.186 | 0.372 |
| Purified water[5] | Qs | qs | qs |
| Film coated tablet weight | 223.6 | 335.4 | 670.8 |

[1]The salt factor is 1.272. The drug substance quantity is increased if the content is ≤99.5% with a corresponding reduction in the microcrystalline cellulose content.
[2]Vegetable origin
[3]Excess coating is prepared to compensate for losses during the coating process
[4]The coating premix is a commercially available product
[5]Removed during processing

We claim:

1. A coated tablet comprising a tablet core and an immediate release coating, wherein the tablet core comprises a disintegrant and 254.4 mg ribociclib succinate, and wherein the tablet has a dissolution profile produced according to United States Pharmacopeia (USP) <711> by dissolving the tablet using a rotating basket at 100 rpm at 37° C. in 900 mL of dissolution media of pH 1 HCl, pH 2 HCl, pH 4.5 acetate buffer, or pH 6.8 phosphate buffer, wherein the dissolution profile corresponds to FIG. 4, wherein LEE011 is ribociclib.

2. The tablet of claim 1, wherein the tablet core comprises at least 40% ribociclib succinate (w/w).

3. A coated tablet comprising a tablet core and an immediate release coating, wherein the tablet core comprises a disintegrant and 254.4 mg ribociclib succinate, the tablet releases at least 75% of the ribociclib after 40 minutes and releases less than 75% of the ribociclib after 20 minutes, when testing dissolution of the tablet according to United States Pharmacopeia (USP) <711>, using a method with a rotating basket at 100 rpm at 37° C. in 900 mL of dissolution media at pH 1 HCl, pH 2 HCl, pH 4.5 acetate buffer, or pH 6.8 phosphate buffer.

4. The tablet of claim 3, wherein the tablet comprises at least 40% ribociclib succinate (w/w).

* * * * *